United States Patent
Ganey

(10) Patent No.: US 10,646,618 B2
(45) Date of Patent: May 12, 2020

(54) BONE GRAFT

(71) Applicant: Timothy Ganey, Tampa, FL (US)

(72) Inventor: Timothy Ganey, Tampa, FL (US)

( * ) Notice: Subject to any disclaimer, the term of this patent is extended or adjusted under 35 U.S.C. 154(b) by 141 days.

(21) Appl. No.: 16/037,278

(22) Filed: Jul. 17, 2018

(65) Prior Publication Data

US 2018/0318465 A1 Nov. 8, 2018

Related U.S. Application Data

(62) Division of application No. 13/888,655, filed on May 7, 2013, now Pat. No. 10,046,089, which is a division
(Continued)

(51) Int. Cl.
*A61F 2/28* (2006.01)
*A61L 27/34* (2006.01)
(Continued)

(52) U.S. Cl.
CPC ............. *A61L 27/34* (2013.01); *A61F 2/28* (2013.01); *A61F 2/30771* (2013.01); *C12N 5/0662* (2013.01); *C12N 5/0663* (2013.01); *C12N 5/0664* (2013.01); *C12N 5/0665* (2013.01); *C12N 5/0666* (2013.01); *C12N 5/0667* (2013.01); *C12N 5/0668* (2013.01); *E05F 15/42* (2015.01); *A61F 2/3094* (2013.01); *A61F 2002/2835* (2013.01); *A61F 2002/30062* (2013.01); *A61F 2002/3092* (2013.01); *A61F 2002/30331* (2013.01); *A61F 2002/30604* (2013.01); *A61F 2002/30838* (2013.01);
(Continued)

(58) Field of Classification Search
CPC .. A61F 2/28; A61F 2002/2835; A61F 2/2846; A61F 2002/30971; A61F 2002/30838; A61F 2002/3084; Y10T 156/1041; C12N 2535/10
See application file for complete search history.

(56) References Cited

U.S. PATENT DOCUMENTS 3,852,045 A 12/1974 Wheeler et al.
5,112,354 A 5/1992 Shires
(Continued)

FOREIGN PATENT DOCUMENTS

EP 2338530 6/2011
WO 9939757 8/1999
(Continued)

OTHER PUBLICATIONS

St. John T.A., et al., Physical and Monetary Costs Associated With Autogenous Bone Graft Harvesting, Am. Journal of Orthopedics; 32:18-23, 2003.
(Continued)

*Primary Examiner* — David H Willse
*Assistant Examiner* — Javier G Blanco
(74) *Attorney, Agent, or Firm* — David L. King

(57) ABSTRACT

The present invention relates to a novel bone graft and methods for producing said graft. Said bone graft can be used for surgical, plastic and/or cosmetic bone replacement for a patient in need thereof. The bone graft is made of a scaffold or matrix of sheet material having a 3-dimensional pattern of a continuous network of voids and/or indentations for enhancing new bone growth.

10 Claims, 7 Drawing Sheets

Related U.S. Application Data of application No. 13/303,811, filed on Nov. 23, 2011, now Pat. No. 8,535,388.

(51) Int. Cl.
*C12N 5/0775* (2010.01)
*A61F 2/30* (2006.01)
*E05F 15/42* (2015.01)

(52) U.S. Cl.
CPC ............... *A61F 2002/30971* (2013.01); *C12N 2525/00* (2013.01); *Y10T 156/10* (2015.01); *Y10T 156/1041* (2015.01); *Y10T 156/1052* (2015.01); *Y10T 156/12* (2015.01)

(56) References Cited

U.S. PATENT DOCUMENTS

| | | | |
|---|---|---|---|
| 5,282,861 | A | 2/1994 | Kaplan |
| 6,419,491 | B1 | 7/2002 | Ricci |
| 7,018,418 | B2 | 3/2006 | Amrich et al. |
| 7,208,222 | B2 * | 4/2007 | Rolfe ...................... A61F 2/442 428/304.4 |
| 7,820,871 | B2 | 10/2010 | Xu |
| 7,901,462 | B2 | 3/2011 | Yang et al. |
| 2003/0059742 | A1 | 3/2003 | Webster et al. |
| 2003/0118692 | A1 | 6/2003 | Wang et al. |
| 2003/0125739 | A1 | 7/2003 | Bagga et al. |
| 2005/0100578 | A1 | 5/2005 | Schmid |
| 2005/0112397 | A1 | 5/2005 | Rolfe |
| 2005/0221703 | A1 | 10/2005 | Stone |
| 2005/0272153 | A1 | 12/2005 | Xuenong et al. |
| 2006/0141012 | A1 * | 6/2006 | Gingras ...................... A61F 2/08 424/442 |
| 2006/0229735 | A1 * | 10/2006 | Roy ...................... A61F 2/0077 623/23.74 |
| 2008/0020012 | A1 | 1/2008 | Ju et al. |
| 2009/0092674 | A1 | 4/2009 | Ingram |
| 2010/0036502 | A1 | 2/2010 | Svrluga |
| 2010/0112032 | A1 | 5/2010 | Guelcher |
| 2010/0221835 | A1 | 9/2010 | Tanaka et al. |
| 2010/0249947 | A1 | 9/2010 | Lesh |
| 2010/0331865 | A1 * | 12/2010 | Bradica ...................... A61F 2/28 606/151 |

FOREIGN PATENT DOCUMENTS

| | | |
|---|---|---|
| WO | 2006044832 | 4/2006 |
| WO | 2008115160 | 9/2008 |

OTHER PUBLICATIONS

Olson G.B., Computational Design of Hierarchically Structured Materials, Science; 277: 1237-1242, 1997.
Liao H., et al., Response ofrat osteoblast-like cells to microstructured model surfaces in vitro, Biomaterials 24: 649-54, 2003.
Clover J. and Dodds R.A., Integrin subunit expression by human osteoblasts and osteoclasts in situ and in culture, J. Cell Sci; 103: 267-271, 1994.
Ingber D.E., Cellular Tensegrity: Exploring How Mechanical Changes in the Cytoskeleton Regulate Cell Growth, Migration, and Tissue Pattern during Morphogenesis, Int. Rev. Cytol.; 150: 173-224, 1994.
Meazzini MC et al., Osteoblast Cytoskeletal Modulation in Response to Mechanical Strain In Vitro, J. Orthop. Res.; 16: 170-180, 1998.
Ingber D.E., Tensegrity: The Architectural Basis of Cellular Mechanotransduction, Annu. Rev. Physiol.; 59: 575-599, 1997.
Bindermann I., et al., The Transduction of Mechanical Force into Biochemical Events in Bone Cells May Involve Activation of Phospholipase A2, Calcif Tissue Int.; 42: 261-266, 1988.
Somjen D., et al., Bone Remodeling Induced by Physical Stress Is Prostaglandin E2 Mediated, Biocim. Biophys. Acta; 627: 91-100, 1980.
Kurtz, Steven M; Devine, John N; PEEK biomaterials in trauma, orthopedic and spinal implants, Aug. 7, 2007, Biomaterials, 28, 4845-4869.
Nikolovski J., et al., Cyclic strain inhibits switching of smooth muscle cells to an osteoblast-like phenotype; FASEB J.; 17: 455-7, 2003.
Rozengurt E., et al., Cyclic AMP: A mitogenic signal for Swiss 3T3 cells, J. Cell Biol.; 78: 4392-4396, 1981.
Shen V., et al., Prostaglandins Change Cell Shape and Increase Intercellular Gap Junctions in Osteoblasts Cultured From Rat Fetal Calvaria, J. Bone Miner Res.; 1: 2443-249, 1986.
Chen C.S., et al., Geometric Control of Cell Life and Death, Science; 276: 1425-1428, 1997; Edmondson A.G., Bosten, 1987.
Jee W.S.S., et al., Effects of spaceflight on trabecular bone in rats, Am. J. Physiol.; 244: R310-R314, 1983.
Zerath E., et al., Effects of spaceflight on bone mineralization in the rhesus monkey, J. Appl. Physiol.; 81: 194-200, 1996.
Backup P.K., et al., Spaceflight results in reduced mRNA levels for tissue-specific proteins in the musculoskeletal system, Am. J. Physiol.; 266: E567-E573, 1994.
Holick, M.F.; Perspective on the Impact of Weightlessness on Calcium and Bone Metabolism; Bone Bol. 22, No. 5 Supplement May 1998: 105S-111S.
Caillot-Augusseas A., Lafage-Proust MH et al., Bone formation and resorption biological markers in cosmonauts during and after a 180-day spaceflight (Euromir 95), Clin. Chem.; 44: 578-585, 1998.
Sampath T.K. and Reddi A.H., Distribution of bone inductive proteins in mineralized and demineralized extracellular matrix, Biochem Biophys. Res. Commun.; 119: 949-54, 1984.
Ganey T.M., et al., Trabecular Parameters in Whale: Examining Naive Trabecular Conformation; 44th Annual Meeting, New Orleans, Louisiana, Orthopaedic Research Society, Mar. 16-19, 1998.
Harris.A., et al., Effects of Orbital Spaceflight on Human Osteoblast Cell Physiology and Gene Expression, Bone 20 (4) 26: 325-31, 2000.
Reddi A.H. and Huggins C.B., Proc. Soc. Exp. Biol. Med.; 143: 634-637, 1973.
Sampath T.K. and Reddi A.H., Importance of Geometry of the Extracellular Matrix in Endochondral Bone Differentiation, J. Cell. Biol.; 98: 2192-2197, 1984.
Borden M., et al., Structural and human cellular assessment of a novel microsphere-based tissue engineered scaffold for bone repair, Biomaterials; 24: 597-609, 2003.
Koob T.J., et al., Biocompatibility of NOGA-polymerized collagen fibers I. Evaluation of cytotoxicity with tendon fibroblasts in vitro, J. Biomed. Mat. Res.; 56: 31-39, 2001.
Koob T.J. and Hernandez D.J., Material properties of polymerized NOGA-collagen composite fibers: development of biologically based tendon constructs, Biomaterials; 23: 203-212, 2002.
Suzuki F. Roles of cartilage matrix proteins, chondromodulin-1 and -II, in endochondral bone formation: a review. Connect Tissue Res. 1996;35(1-4):303-7.
Gamradt SC, Lieberman Jr. Genetic modification of stem cells to enhance bone repair. Ann Biomed Eng. Jan. 2004;32(1):136-47.
Sammarco VJ, Chang L. Modern issues in bone graft substitutes and advances in bone tissue technology. Foot Ankle Clin. Mar. 2002;7(1):19-41.
Department of Health and Human Services, 2. Jul. 2002; http://www.fda.gov/cdrh/mda/does/p000058.pdf.
Sikavitsas V.I., et al., Formation of three-dimensional cell/polymer constructs for bone tissue engineering in a spinner flask and a rotating wall vessel bioreactor, J. Biomed. Mat. Res.; 62: 136-146, 2002.
Jaiswal N., et al., Osteogenic Differentiation of Purified, Culture-Expanded Human Mesenchymal Stem Cells In Vitro, J. Cell Biochem.; 64: 295-312, 1997.
West D.C., et al., A Simplified in Situ Solubilization Procedure for the Determination of DNA and Cell Number in Tissue Cultured Mammalian Cells. Anal. Biochem.; 147: 289-295, 1985.
Koob T.J., et al., Biocompatibility of NOGA-polymerized collagen fibers II. Attachment, proliferation, and migration of tendon fibroblasts in vitro, J. Biomed. Mat. Res.; 56: 40-48, 2001.

(56) References Cited

OTHER PUBLICATIONS

Tavakoli M., et al; The use of power beams in surface modification, Medical Device Technology, vol. 18 No. 1, Jan.-Feb. 2007: TWI Ltd, 2007.
Elias Carlos Nelson, Titanium dental implant surfaces, Materia (Rio J.) vol. 15 No. 2 Rio de Janeiro 2010, online version ISSN 1517-7076.
Alekhin A.P., et al; Structural properties of the titanium dioxide thin films grown by atomic layer deposition at various numbers of reaction cycles, Applied Surface Science 257 (2010) 186-191.
Yeh, Chih-Ko and Rodan, Gideon A, Tensile Forces Enhance Prostaglandin E Synthesis in Osteoblastic Cells Grown on Collagen Ribbons, Dept of Oral Biology, University of Connecticut Health Center, Calcified Tissue International (1984) 36: S67-S71.
Ogden, John A; Skeletal Injury in the Child, Third Edition, Springer 2000; pp. 5-6.
Schieker, Mattias et al; Biomaterials as Scaffold for Bone Tissue Engineering; European Journal of Trauma 2006, No. 2, Urban and Vogel, pp. 114-124.

* cited by examiner

BONE GRAFT

RELATED APPLICATIONS

This application is a division of U.S. Ser. No. 13/888,655 filed on May 7, 2013 which is a division of U.S. Ser. No. 13/303,811 filed on Nov. 23, 2011 entitled "Bone Graft" now U.S. Pat. No. 8,535,388 issued on Sep. 17, 2013.

FIELD OF THE INVENTION

The present invention relates to a novel bone graft and methods for producing said graft. Said bone graft can be used for surgical, plastic and/or cosmetic bone replacement for a patient in need thereof or used as a means of delivering medicaments and defining marrow constituents.

BACKGROUND OF THE INVENTION

Orthopaedic surgeons have been applying the principles of tissue engineering for years, while transplanting and shifting matrices within patients to promote regenerative potential. The advent of new technology now offers even greater promise and brings unbridled enthusiasm that full regenerative potential of tissue and whole organ systems can be achieved in the near future. While soft tissue repair can be managed by achieving scar tissue replacement, such outcome in most orthopaedic applications and indications would be insufficient. Bone requires a tissue-specific composition to be attendant to function for skeletal support. The forming of collagenous material alone, even if vascularized, will fail to meet the biophysical demands of repetitive skeletal loading and be inadequate.

Implicit in the goals of repairing bone are to achieve restitution of space, mechanical solidity, and functional continuity. Often the biological signals do not provide sufficient stimulus to attain a full repair. Orthopaedic interventions to alleviate fracture non-union, pseudarthrosis, and scoliosis; bone defects due to congenital or developmental anomalies, infection, malignancy, or trauma often require bone grafting to augment the process of bone healing. The therapeutic goal of graft material is to omit compliance features such as strain tolerance, reduced stiffness, and attenuated strength, and instead promote primary, or membranous-type bone formation within the physical approximation of graft material. In order to achieve this, three basic components are required: osteoprogenitor cells, osteoinductive factors, and an osteoconductive matrix or scaffold.

Autologous cancellous bone remains to date the most effective graft material, where osteoinductivity, osteoconductivity, and a rich source of cells endow the material with not only biological activity but a degree of immunologic transparency as well. Because of complications and shortcomings associated with autogenous grafting that include limited quantity, donor-site morbidity, and more recently cost consideration (St. John T. A., et al., Am. Journal of Orthopedics; 32:18-23, 2003), numerous alternative graft materials have been developed for orthopaedic applications. All references as cited herein are incorporated in their entireties for the purposes of the present invention.

Allograft bone is used extensively as a material bridge to osseo-integration, acknowledged as a substitute for the general short supply of autograft. Primary uses to date have been in spine, although both trauma and plastics account for a growing market. The market offers several options, the most valuable being the machined components for surgical implantation. Over 675,000 procedures set the demand for allograft annually, with a projected market growth set at 19%.

Available grafting substitutes include cancellous and cortical allograft bone ceramics such as sintered coralline matrices, hydroxyapatite and tri-calcium phosphate, demineralised bone matrix, bone marrow, composite polymer grafts, and recently recombinant cytokines with collagen carriers. Complications include availability, cost, variable bioabsorption, brittleness, immune stimulation, and regulatory hurdles.

The shape of the biomaterial template is critical to the success of manufacturing. A central tenet of biomineralization is that nucleation, growth, morphology and aggregation of the inorganic crystals of bone are regulated by organized assemblies of organic macromolecules. The close spatial relationship of hydroxyapatite crystals with Type I collagen fibrils in the early stage of bone mineralization is a relevant example. It is equally evident that combining hydroxyapatite with protein does not render the macroscopic form of bone nor impart its characteristic properties. Unlike fabricated materials that can be developed from components with predictable properties (Olson G. B., Science; 277: 1237-1242, 1997), biological systems control desired properties by utilizing an intrinsic rationale that discriminates essential from non-essential factors. Living organisms avoid the geometric frustration of randomness by segregating structures that resonate function.

Future envisaged bio-engineering strategies will combine several favourable properties of the current items in an effort to achieve hybrid materials that support tissue differentiation without shielding capacity for integrated modelling.

Ideally, new materials will provide tissue compatibility and minimize patient morbidity.

Although bone can appear de novo, it more often develops from accretion on a scaffold of matrix that contains appropriate vascular and compositional arrangement. As such, both 2-dimensional and 3-dimensional patterns have been shown to enhance osteoconductivity (Liao H., et al., Biomaterials 24: 649-54, 2003). Bone has significantly more matrix than cells, and cell regulation through anchorage dependent mechanisms is an established premise (Clover J. and Dodds R. A., J. Cell Sci; 103: 267-271, 1994; Ingber D. E., Int. Rev. Cytol.; 150: 173-224, 1994; Meazzini M C et al., J. Orthop. Res.; 16: 170-180, 1998). Compensatory mechanisms for changing sensitivity to mechanical stimulation have been shown to undergo adaptive or kinetic regulation, likely tied, directly to osteoblast attachment to immobilized molecules in the extracellular matrix (ECM). ECM molecules promote cell spreading by resisting cell tension, thereby promoting structural rearrangements within the cytoskeleton (Ingber D. E., Annu. Rev. Physiol.; 59: 575-599, 1997). Several lines of evidence suggest that tension or mechanical stretch exerts a direct positive effect on bone cells and bone cell differentiation through: 1.) activation of phospholipase A2, 2.) release of arachidonic acid; 3.) increased prostaglandin E synthesis, 4.) augmented cyclic adenosine monophosphate (cAMP) production; and 5.) and expression of the bone associated transcription factor CBFA-1 (Bindermann I, et al., Calcif Tissue Int.; 42: 261-266, 1988; Somjen D., et al., Biocim. Biophys. Acta; 627: 91-100, 1980; Yeh C. K. and Rodan G. A., Calcif Tissue Int.; 36: S82-85, 1984; Nikolovski J., et al., FASEB J.; 17: 455-7, 2003). It has long been recognized that a sustained increase in the cellular level of cAMP constitutes a growth-promoting signal (Rozengurt E., et al., J. Cell Biol.; 78: 4392-4396, 1981), and that prostaglandins directly affect a change in cell shape and increase intercellular gap junctions (Shen V., et al., J. Bone Miner Res.; 1: 2443-249, 1986). Without a capacity for attachment and spreading, cells undergo apoptosis, or programmed cell death (Chen C. S., et al., Science; 276: 1425-1428, 1997; Edmondson A. C., Bosten, 1987).

Bone withstands compressive loading by efficient distribution of internal tensile forces. Bone cells do however adhere to structures that can resist compression in order to spread, engaging osteoblast attachment, mineralization, and bone matrix organization as linked processes. Even though deformation at the tissue level might be evaluated as an ability to resist compression, force along individual trabeculae reflects an ordinate of new tension. Under normal cycles of development, increased mass conveys a progressive stimulus of tension to cells, gravity imposing a unidirectional vector to terrestrial life.

A sudden reduction in gravity imposes serious consequence to the skeleton. As shown by studies of astronauts, marked skeletal changes in the weight-bearing skeleton including a reduction in both cortical and trabecular bone formation (Jee W. S. S., et al., Am. J. Physiol.; 244: R310-R314, 1983), alteration in mineralization patterns (Zerath E., et al., J. Appl. Physiol.; 81: 194-200, 1996), and disorganization of collagen and non-collagenous protein metabolism (Backup P. K., et al., Am. J. Physiol.; 266: E567-E573, 1994) have been associated with microgravity. Each month of spaceflight results in a 1-2% reduction of bone mineral density that has been linked to down-regulated PTH and 1,25-dihydroxyvitamin D3 production (Holick M F, Bone; 22: 105S-111S, 1998). Indices from cosmonauts aboard Euromir 95 account bone atrophy to both a reduction in bone formation and increased resorption. PTH decreased (48%), as did bone alkaline phosphatase, osteocalcin, and type-I collagen propeptide. At the same time bound and free deoxypyridinoline and pro-collagen telopeptide increased (Caillot-Augusseas A., Lafage-Proust M H et al., Clin. Chem.; 44: 578-585, 1998). The chords of information establish a role for microgravity in uncoupling bone formation and enhancing resorption.

If exposure to microgravity demonstrates physiologic responses that mirror a reduction in trabecular tension, then would reciprocity of function be expected in bone that is modelled under microgravity and then exposed to normal gravitational force? Prolonged weightlessness, as experienced in space flight effectively unloads the skeleton, relaxing tension on the trabeculae. In this manner, osteoblast physiology preferably is altered due to attachment perturbations. Conversely, a bioscaffold modelled in the form of tissue that has developed under microgravity, will experience an enhanced tensile loading sensation on individual trabeculae.

In view of the above it is therefore the object of the present invention is to provide a scaffold that preferably is not only structurally enhancing but at the same time inductively optimum for bone formation. This graft should be designed to stimulate cell differentiation and bone regeneration, and to be utilized as an orthotopic alternative to tissue transplantation.

SUMMARY OF THE INVENTION

The present invention overcomes the disadvantages of the art as described above and, in a first aspect of the invention, provides a sheet material for a bone matrix scaffold, comprising a surface pattern that is enhancing osteo-conductivity, wherein the surface pattern is a 3-dimensional substantially continuous network having voids, or surface indentations that may or may not penetrate the sheet.

In the context of the present invention, the term "enhancing osteo-conductivity" shall mean the ability to change surface roughness, engage surface energy, promote mimetic patterns that resolve randomness and integrate form and functional regenerative clues, that might also include appropriate bioactive regenerative adjuvants such as proteins, peptides, charge, shape, size, allometry, isotropy, anisotropy, or non-biologic energies such as electric field, vibrational energy, gravitational variation, pressure wave, or material compositions that would enhance tissue attachment and reduce proliferative response.

In a preferred sheet material according to the present invention, the sheet has a thickness of about 150 micron. The voids can preferably have a medium width of about 10 microns, and at least 10% of said voids have a fractal dimension of at least 3. The sheet can be thicker and the value of the invention is the surface regularity. In purpose, the sheet could be between 150 micron and 2 mm in thickness, with surface indentations ranging from 10 micron to 150 micron. Neither side of the sheet need be mirrored (as in image), and depth of indentations can vary by location to best accommodate geometric form.

Even more preferred is a sheet material according to the present invention, wherein the sheet is made of a biological cellular, cellular as a source of its production, or in containing cell fragments to promote regenerative cues, material hereinafter referred to as a biomaterial, preferably consisting essentially of collagen. Herein, "essentially" shall mean that more than 95% of the initial material of the structure, preferably more than 98%. Among the wide variety of substrates that could be used as a basis for cultured allograft, collagen uniquely supports several desirable features. First, collagen is a principal component of bone, contributing more than 90% to the organic composition. Second, in studies demonstrating osteoinductive capacity of demineralised bone matrix, 60% of the stimulatory activity is derived from the collagen-associated component (Sampath T. K. and Reddi A. H., Biochem Biophys. Res. Commun.; 119: 949-54, 1984). Third, human collagen has been approved for injection and demonstrates minimal immunoreactivity. Nevertheless, the use of other collagens and other sources of collagen (e.g. chicken, etc.) are envisaged as well. Another embodiment of the material would include ceramics, non-organic materials, electrospun nanofilaments, and nanoceramic crystals that might be either polarized, or aligned by their fabrication to a microelectrical preference.

In another embodiment of the present invention, the material of the sheet is essentially biodegradable, bioerodable and/or bioresorbable. "Biodegradable, bioerodable and/or bioresorbable and/or bioinstructive" in the context of the present invention shall mean capable of being decomposed by organisms, in particular the human body. Furthermore, the sheet material shall be able to decay naturally and harmlessly into parts that are resorbable by organisms, in particular the human body. "Essentially" shall mean that more than 95% of the initial material of the structure is decomposed, preferably more than 98%.

The invention duplicates the architecture of under-modelled cancellous bone, guided by the idea that a material later populated with bone cells will more quickly respond to the mechanicals and biological roles of bone with subsequent loading. Because cancellous bone is a porous structure, its mechanical properties are dependent upon the distribution and arrangement of its structural elements, or trabeculae. Considering three-dimensional architecture to be critical to the mechanical integrity of trabecular bone, the applicant established the morphometry of under-loaded marine mammal tissue (Ganey T. M., et al., 44th Annual Orthopaedic Research Society, 1998). The rationale for the present approach is based on the observation that prenatal cancellous bone in humans has unique potential for rapid postnatal modelling (Ogden L A., Springer Verlag, 1999), and that cell-culture studies performed during orbital space flight demonstrate significant osteoblast stimulation upon return to increased gravitational field (Harris S. A., et al., Bone 20(4) 26: 325-31, 2000). In the case of sea mammals, separate environment buoyancy suppresses loading variation, resulting in minimal secondary bone formation and modelling. Whale bone retains a primary trabecular structure and does not remodel according to standard parameters of mechanical adaptation. Trabecular morphology and osteocyte number are similar among commonly oriented blocks, while significant differences can be demonstrated between tissue sections studied in planes perpendicular to the axial length of bones.

TABLE 1

| BIOPSY | BV/TV | BS/BV | TbTh | TbSp | TbN | Ost# |
|---|---|---|---|---|---|---|
| Cross | 17.71 | 14.98 | 135.16 | 631.70 | 1.33 | 230/mm$^2$ |
| Long | 24.64 | 8.67 | 231.05 | 710.09 | 1.06 | 150/mm$^2$ |

BV/TV—Bone Volume/Tissue Volume;
BS/BV—Bone Surface/Bone Volume;
TbTh—Trabecular Thickness = μm;
TbN—Trabecular Number;
Ost #—osteocyte cells per mm$^2$ Bone examined in longitudinal dimension demonstrated greater trabecular separation, thicker trabeculae, yet because of the lesser number of trabecula, still structured less bone surface per volume of tissue. Although bone surface to bone volume, trabecular thickness, and trabecular number followed predicted allometric extrapolation, reflected in greater trabecular separation and reduced trabecular number. It is this separation and thickness that provides a basis for bio-reactor cell culture and offers the chance to manufacture bone as claimed in this application.

Reddi and Huggins demonstrated the effect of open-ended vs. close-ended tubes on cell differentiation, showing bone rather than cartilage as the respective outcome (Reddi A. H. and Huggins C. B., Proc. Soc. Exp. Biol. Med.; 143: 634-637, 1973), and further confirming the importance of particle size in the activity of demineralised bone matrix (Sampath T. K. and Reddi A. H., J. Cell. Biol.; 98: 2192-2197, 1984). Still other studies have shown the importance of geometry when considering the effective integration of an implant, particularly the porosity and interconnections of the matrix (Borden M., et al., Biomaterials; 24: 597-609, 2003). To assure that the type-I collagen matrix will maintain its structure during the cell culture process and avoid the toxicity of other cross-linking agents, a non-aldehyde cross-linking process preferably is utilized to stabilize the construct (Koob T. J., et al., J. Biomed. Mat. Res.; 56: 31-39, 2001; Koob T. J., et al., J. Biomed. Mat. Res.; 56: 40-48, 2001). Previous work by Koob and Hernandez determined that pepsin-solubilized type-I collagen fibers can be polymerized with nordihydroguaiaretic acid (NDGA), and plant compound with antioxidant properties. In tendon, the process produces fibers with material properties in uniaxial tensile tests to failure that are comparable to native tendon (Koob T. J. and Hernandez D. J., Biomaterials; 23: 203-212, 2002).

The role of scaffold material as a delivery vehicle for osteogenic materials is best understood in the context of bridging critical-size defects. Among the key roles of the sheet material and scaffold is to optimize the location and release of the biogenic factors while insulating the space from soft-tissue encroachment. Methods for design and development of collagen-based bone prostheses have focused on cross-lining agents in order to improve the tensile properties of the collagenous constructs and to reduce the potential inflammatory response to foreign materials. Optimizing the geometry of the prosthesis is a critical engineering strategy for assuring matrix deposition, and cross-linking of the collagen matrix (sheet material) supports the interim scaffold to effect cell attachment.

The concept for manufactured graft, in particular bone allograft, depends on a capacity to achieve reproducible design in a geometric scaffold. Such scaffolds will support osteoblast attachment and permit bone-specific matrix production. In light of anticipated rulings by the FDA for greater control of tissue products for transplantation, developing alternative materials with comparable osteoinductivity seems appropriate. Several features combine to make this invention unique; first, the bone model for the sheet material and scaffold architecture approximates an under-modelled mammal, using increased porosity to accelerate ingrowth; second, a unique cross-linking methodology reduces the bioabsorption rate of polymers (e.g. human collagen) and effects a mechanically competent scaffold; and third, osteoblasts can be used to deposit a bone matrix onto the scaffold that will make it osteo-inductive.

The controlled process according to the present invention is intended to take advantage of previous regulatory considerations of human collagen as a device. FDA approval for human collagen in combination with incipient material is not unprecedented and will lower the threshold for marketability.

Another aspect of the present invention is thus directed to a method for producing a sheet material for bone grafts, comprising the steps of a) providing a rectangular sheet of suitable biomaterial, and b) introducing a surface pattern into said suitable biomaterial, wherein said surface pattern is enhancing the osteo-conductivity of said biomaterial and is a 3-dimensional substantially continuous network having voids. Preferably said method produces a sheet that has a thickness of about 150 micron. Nevertheless, thinner sheets can be produced that are to be used in laminate structures, these thinner sheets are herein designated as "thin wafers". A preferred thickness of such wafers preferably is between 150-300 nm and the individual fibers attending the sheet fabrication preferably range from 50-150 nm. These individual sheets will be by design variable in porosity but accountable to isotropic layering so that fundamental randomness to directed loading isretained.

More preferred is a method according to the present invention, wherein said biomaterial is collagen, in particular type-I collagen, derived from suitable sources as indicated above.

Generally, the surface pattern of the inventive sheet material can be provided to said sheet material by all suitable techniques that allow for the introduction of a surface pattern having the correct dimensions. Preferred is a method according to the present invention, wherein said surface pattern is introduced by etching and/or embossing and/or microprinting the surface or surfaces of the biomaterial. The surface pattern provides for a substantially continuous network having voids and enhances the osteo-conductivity of the biomaterial and is a 3-dimensional network. One example of the surface pattern can be derived from FIG. 1.

More preferred is a method according to the present invention, wherein said embossing of the surface or surfaces of the biomaterial is performed by rolling the material in a suitable roller press. Most preferred is a method according to the present invention, wherein voids (e.g. channels and indentations) are introduced having a medium width ranging from 30 microns as a minimal to widths approaching 230 micron in cross dimension. As used herein, a void can be an opening through the sheet 2 or an indentation extending from the outer surface, but not through the sheet 2, the indentations can be hollow depressions or dips or elongated channels all of which make up the network of voids.

In yet another aspect of the method according to the present invention further said method comprises the subsequent and/or intermediate steps of drying (e.g. freeze-drying) said biomaterial and/or storing of said biomaterial, preferably storing under vacuum (e.g. vacuum-packaged).

Yet another aspect of the present invention relates to a bone matrix scaffold comprising at least one sheet material as described above, wherein said at least one sheet material forms a macrostructure having a substantially continuous network and voids as described above. In a particular embodiment of the present invention, the inventive bone matrix scaffold comprises at least two sheets of material. More preferred is a bone matrix scaffold according to the present invention, comprising a laminate structure consisting of said at least two sheets of material.

In another embodiment of the bone matrix scaffold according to the present invention, said network is semi-solid, in particular forming a gel. Preferably, said bone matrix scaffold according to the present invention furthermore comprises crosslink-structures. More preferably, said crosslink-structures comprise at least one polymer and/or a mixture of polymers. According to one embodiment of the bone matrix scaffold according to the present invention said at least one polymer can be copolymer having carboxylic acid groups and/or amine groups. The at least one polymer can be conductive polymer selected from polypyrrole, polyaniline, polyacetylene, and/or polythiophene. These conductive polymers can be laminated in sheets with insulating layers between or interpositioned with the conductive sheets to separate charge and define voltage stacks in the poly-laminates. The insulating layers can be polyurethane sheets or layers or a bioabsorbable insulation layer of a net neutral charge material.

Most preferred is a bone matrix scaffold according to the present invention, wherein said crosslink-structures comprise collagen fibers. Optimally, said crosslink-structures comprise non-aldehyde cross-linked type I collagen. In a particular embodiment of the bone matrix scaffold according to the present invention, said crosslink-structures form spokes and/or mimic cell microfilaments. Schematic examples of the structures of these particular embodiments can be taken from the accompanying figures. In yet another particular embodiment of the bone matrix scaffold according to the present invention, wherein said collagen is chemically cross-linked with nordihydroguaiaretic acid or other suitable agents to confer stability.

The bone matrix scaffold according to the present invention can have a surface area of at least 1 m$^2$/g. Preferably, the voids of said macrostructure of the bone matrix scaffold according to the present invention are substantially continuous. Thus, preferred is a bone matrix scaffold according to the present invention, wherein at least 10% of said voids of said macrostructure are connected (are in contact with) said voids of said sheet material. Thus, a network is formed that can be 3-dimensional throughout the bone matrix scaffold according to the present invention. Nevertheless, in other particular applications, it might be suitable to provide a bone matrix scaffold according to the present invention, wherein said voids of said macrostructure and said voids of said sheet material are not connected.

In another embodiment of the bone matrix scaffold according to the present invention, said voids of said macrostructure define openings and the average diameter of said openings and the average diameter of a cross-section of the network have a ratio of from 2:1 to 10:1. Preferred is a bone matrix scaffold according to the present invention, wherein the ratio is from 2:1 to 5:1.

In yet another embodiment of the bone matrix scaffold according to the present invention, wherein the network of a cubic portion of said matrix has dimensions of 0.5 cm on all sides and voids defining openings with an average diameter of 50-500 µm, and a connective number of at least 10. Preferred is a bone matrix scaffold according to the present invention, wherein the connective number is at least 20.

In yet another embodiment of the bone matrix scaffold according to the present invention, wherein a cross section of said network has a maximum and minimum diameter, with a ratio of the maximum and minimum diameter of from 1:1 to 10:1.

Preferred is a bone matrix scaffold according to the present invention, wherein less than 10% of said voids of said macrostructure have a fractal dimension higher than 1.

According to a preferred embodiment of the bone matrix scaffold according to the present invention, the exterior surface of said scaffold is porous. More preferably, the bone matrix scaffold according to the present invention has a porosity of at least about 20%.

Similar to the sheet material as above, also the bone matrix scaffold is essentially biodegradable, bioerodable and/or bioresorbable and/or bioinstructive. The same definitions as above apply.

According to a preferred embodiment of the bone matrix scaffold according to the present invention, the bone matrix scaffold is essentially permeable to body fluids and/or cells. In yet another aspect of the bone matrix scaffold according to the present invention, the bone matrix scaffold further comprises cells and/or proteins. Said cells can be selected from the group of living cells and recombinant cells, chondrocytes, growth factor producing cells, such as TGF FGF-producing cells, and osteoblasts, and the proteins are selected from proteins that inhibit or enhance vascularization, enhance or retard innervation. These proteins are well known to the person of skill and described in the literature, e.g. in Suzuki F. Roles of cartilage matrix proteins, chondromodulin-I and —II, in endochondral bone formation: a review. Connect Tissue Res. 1996; 35(1-4):303-7 and the references as cited therein.

According to a preferred embodiment of the bone matrix scaffold according to the present invention, the size of said matrix scaffold changes less than 50% when said cells are added to the matrix. More preferred, the bone matrix scaffold according to the present invention has a compressive modulus of at least 0.4 MPa at 4% strain, and/or a density of less than about 0.150 g/cm$^3$.

Another aspect of the present invention then relates to a method for producing a bone matrix scaffold according to the present invention, comprising the steps of a) providing at least one sheet material according to the present invention having a surface pattern that enhances osteo-conductivity and potentially supports inductivity, the surface pattern is a 3-dimensional substantially continuous network having voids, and b) cross-linking said at least one sheet material using fibers, whereby a macrostructure is formed having a substantially continuous network and voids. Said macrostructure or bone matrix scaffold that is formed is designated herein also as "cell" of the graft material (different from the biological cells as also described herein) or "building block" of the graft of the present invention. In one particular embodiment, a building block comprises two sheets of material that are cross-linked by the method according to the present invention. In one particular embodiment of the method according to the present invention, a laminate structure consisting of said at least two sheets of material is formed.

The method for producing a bone matrix scaffold according to the present invention in one embodiment forms a semi-solid network, in particular a gel. Said gel can consist of either a laminate structure or multiple building blocks as described above. More preferred is a method for producing a bone matrix scaffold according to the present invention, wherein said fibers comprise at least one polymer and/or a mixture of polymers. In one embodiment of the method for producing a bone matrix scaffold according to the present invention, said at least one polymer is a copolymer having carboxylic acid groups and/or amine groups. Most preferred is a conductive polymer selected from polypyrrole, polyaniline, polyacetylene, and polythiophene and mixtures thereof. These conductive polymers can be laminated in sheets with insulating layers between or interpositioned with the conductive sheets to separate charge and define voltage stacks in the poly-laminates. The insulating layers can be polyurethane sheets or layers or a bioabsorbable insulation layer of a net neutral charge material.

Preferred is a method for producing a bone matrix scaffold according to the present invention, wherein said fibers are collagen fibers, in particular non-aldehyde cross-linked type I collagen. According to a more preferred method for producing a bone matrix scaffold according to the present invention, said collagen is chemically cross-linked, in particular with nordihydroguaiaretic acid or other suitable agents to confer stability.

In yet another embodiment of the method for producing a bone matrix scaffold according to the present invention, said voids are formed to define openings and the average diameter of said openings and the average diameter of a cross-section of said network is formed to have a ratio of from 2:1 to 10:1, preferably said ratio is from 2:1 to 5:1.

In yet another embodiment of the method for producing a bone matrix scaffold according to the present invention, less than 10% of said voids of said macrostructure are formed to have a fractal dimension higher than 1.

Preferred is furthermore a method for producing a bone matrix scaffold according to the present invention, wherein the exterior surface of said scaffold is made porous.

Yet another aspect of the method for producing a bone matrix scaffold according to the present invention further comprises the step of incubating said macrostructure with cells for a predetermined period of time. To assure that the matrix deposited on the scaffold is bone specific, both osteoblasts and mesenchymal stem cells preferably are used to further create the bio-scaffold matrix. In choosing a cell line suitable for providing the osteoinductivity of the deposited matrix, it is important that the cells do not in normal culturing conditions spontaneously differentiate into osteoblasts or themselves produce any bone-specific proteins (e.g. alkaline phosphatase). While it is not surprisingly that DBM induces differentiation of confluent human periosteal cells into osteoblast-like cells, the true test of inductivity is demonstrated in that DBM exposure also produces bone-specific response in skeletal muscle myoblast culture (see also below).

Preferred is furthermore a method for producing a bone matrix scaffold according to the present invention, wherein said cells can be selected from the group of living cells and recombinant cells, chondrocytes, growth factor producing cells, such as TGF FGF-producing cells, and osteoblasts, and the proteins are selected from proteins that inhibit or enhance vascularization, enhance or retard innervation. These proteins are well known to the person of skill and described in the literature, e.g. in Suzuki F. Roles of cartilage matrix proteins, chondromodulin-I and —II, in endochondral bone formation: a review. Connect Tissue Res. 1996; 35(1-4):303-7 and the references as cited therein. In still another embodiment, the distillate of material lypholization is collected, and microprinted back on the organic matrix with specific attention to the shape, dimensions, voids, so that a biological imprint of specific design is used to define cell attachment and guide tissue regeneration In another preferred method for producing a bone matrix scaffold according to the present invention, the size of said macrostructure changes less than 50% when said cells are added to the matrix.

Yet another preferred method for producing a bone matrix scaffold according to the present invention further comprises removing said cells from said macrostructure, in order to produce a bone matrix scaffold that can be either used directly, forms an intermediate for other products, is shaped by a suitable technique (as described below for the graft), and/or is used in order to produce a final bone graft, as described below.

Another aspect of the present invention then relates to a bone graft, comprising at least one bone matrix scaffold according to the present invention and osseous and/or chondrial material. In one embodiment, said bone graft according to the present invention comprises at least two bone matrix scaffolds being connected by fibers. Preferably, said fibers comprise at least one polymer and/or a mixture of polymers, more preferably the at least one polymer is a copolymer having carboxylic acid groups and/or amine groups. Most preferred is a bone graft according to the present invention, wherein said at least one polymer is a conductive polymer selected from polypyrrole, polyaniline, polyacetylene, and polythiophene and mixtures thereof.

In yet another embodiment of the bone graft according to the present invention, said fibers are collagen fibers, preferably said fibers are non-aldehyde cross-linked type I collagen. If the fibers are cross-linked, the bone graft according to the present invention comprises collagen that is chemically cross-linked, in particular with nordihydroguaiaretic acid (NDGA).

According to yet another embodiment of the bone graft according to the present invention, said graft is present in the form of a facial and cosmetic surgery graft. Furthermore, the bone graft according to the present invention can be an allograft or autograft.

A preferred bone graft according to the present invention consists essentially of osseous material and/or chondral material. Nevertheless, a bone graft according to the present invention can further comprise osteoinductive substances, preferably, said osteoinductive substances are bone specific growth factors as described herein and known to the person of skill, e.g. from Gamradt S C, Lieberman J R. Genetic modification of stem cells to enhance bone repair. Ann Biomed Eng. 2004 January; 32(1): 136-47, and Sammarco V J, Chang L. Modem issues in bone graft substitutes and advances in bone tissue technology. Foot Ankle Clin. 2002 March; 7(1):19-41 and the references as cited therein.

Yet another aspect of the present invention relates to a method for producing a bone graft according to the present invention, comprising the steps of a) providing at least two bone matrix scaffolds according to the present invention, b) connecting (e.g. cross-linking) said at least two bone matrix scaffolds using fibers, and c) depositing of osseous material and/or chondral material on said connected at least two bone matrix scaffolds.

Preferred is a method for producing a bone graft according to the present invention, wherein said fibers comprise at least one polymer and/or a mixture of polymers, particularly at least one polymer is a copolymer having carboxylic acid groups and/or amine groups, more preferably said at least one polymer is a conductive polymer selected from polypyrrole, polyaniline, polyacetylene, and polythiophene and mixtures thereof.

In yet another aspect of the method for producing a bone graft according to the present invention, said fibers are collagen fibers, preferably said fibers non-aldehyde cross-linked type I collagen. In a preferred method for producing a bone graft according to the present invention, said collagen is chemically cross-linked, in particular with nordihydroguaiaretic acid.

In yet another aspect of the method for producing a bone graft according to the present invention, said depositing of osseous and/or chondrial material comprises incubating said connected at least two bone matrix scaffolds with cells for a predetermined period of time. Said cells can be selected from the group of living cells and recombinant cells, chondrocytes, growth factor producing cells, such as TGF or FGF-producing cells, and osteoblasts, and the proteins are selected from proteins that inhibit or enhance vascularization, enhance or retard innervation. These proteins are well known to the person of skill and described in the literature, e.g. in Suzuki F. Roles of cartilage matrix proteins, chondromodulin-I and —II, in endochondral bone formation: a review. Connect Tissue Res. 1996; 35(1-4):303-7 and the references as cited therein.

A preferred method for producing a bone graft according to the present invention furthermore comprises removing said cells in order to produce a bone graft that can be either used directly, forms an intermediate for other bone-related products, and/or is shaped by a suitable technique (as described below).

Yet another preferred method for producing a bone graft according to the present invention, further comprises shaping the graft, preferably by a method comprising CAD, cutting, moulding and/or pressing. More preferably, the graft is shaped in the form of a facial and/or cosmetic surgery graft. Most preferred is a method for producing a bone graft according to the present invention, wherein the graft is shaped in a patient specific form.

Another method for producing a bone graft according to the present invention further comprises providing osteoinductive substances, in particular proteins, to said graft. Examples are indicated above. Preferably, said osteoinductive substances are bone specific growth factors.

Another aspect of the present invention is then related to a method for surgical, plastic and/or cosmetic bone replacement for a patient, comprising a) providing a graft according to the present invention, and b) implanting said graft into said patient. In said method according to the present invention, the implanting can be performed during cartilage, bone, joint, and/or articular cartilage repair and/or replacement. In a preferred embodiment of the method according to the present invention, said implanting comprises the direct implantation into the matrix of the bone to be replaced.

Preferred is a method for surgical, plastic and/or cosmetic bone replacement according to the present invention, wherein said providing of said graft further comprises shaping the graft, preferably by a method comprising CAD, cutting, moulding and/or pressing. More preferably, the graft is shaped in the form of a facial and/or cosmetic surgery graft. Most preferred is a method for surgical, plastic and/or cosmetic bone replacement according to the present invention, wherein the graft is shaped in a patient specific form, which can then readily be used for the bone replacement treatment. Alternatively, one can use the material as a drug delivery, or cell differentiation incubator. The ability for the poly-laminates to hold specific charge can create a latent charge that functions as a differentiation device, in process, cylinders of porous material, interlaid with autologous patient cells would be implanted in bone, in muscle flaps, in areas of vascular flow and the inherent material charge would not only summon stem cells but partition their pathway towards specific phenotypic expression.

A last aspect of the present invention is then related to a device for producing a sheet material according to the present invention, comprising a device that embosses, etches and/or cuts an osteo-conductive 3-dimensional surface pattern having substantially continuous network having voids into a suitable sheet material. In a preferred embodiment of the present invention, the device according to the present invention comprises compressing rollers.

BRIEF DESCRIPTION OF THE DRAWINGS

The invention is described by way of example and with reference to the accompanying drawings in which.

DETAILED DESCRIPTION OF THE INVENTION

Figure 1:
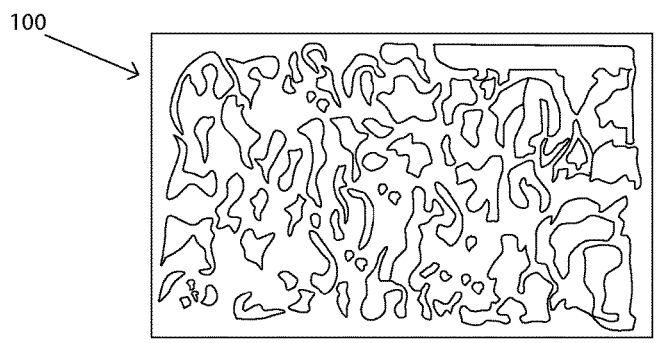
FIG. 1 shows a type-I collagen matrix cut by free-electron laser to reproduce cancellous bone according to the state of the art.

Free-electron Laser etching was used to attempt replication of cancellous bone on varying substrates applied to cell culture plates. The underlying hypothesis, analogous to "building a brick wall", proposes that after setting the first tiers, optimal structure results from subsequent bricks following a precedent of pattern. In this paradigm, the trabecular scaffold represents the foundation of pattern. Although the material 100 was encouraging, insufficient resolution of the laser prevented reproducible fabrication, an important consideration in developing cancellous bone as a manufactured allograft where the structure is intended to confer both physiological and physical characteristics, as illustrated in FIG. 1.

Figure 2:
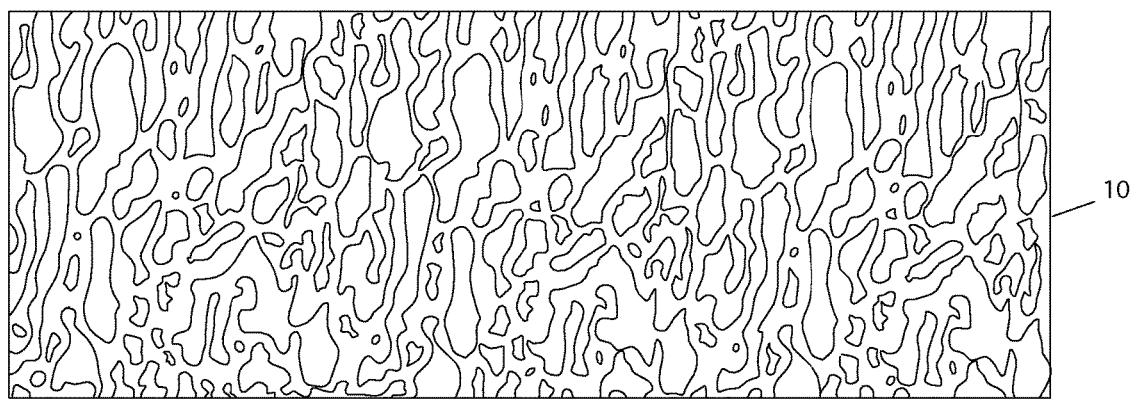
FIG. 2 shows a collagen scaffold representing cancellous bone according to the invention, wherein a tile pattern has been used.
Figure 2A:
FIG. 2A is a photo reproduction of cancellous whale bone, the large portion being of the same scale as shown in FIG. 2, the upper left view being at scale, the lower left view being magnified.
Figure 2A:
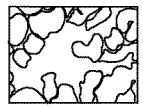
Figure 2A:
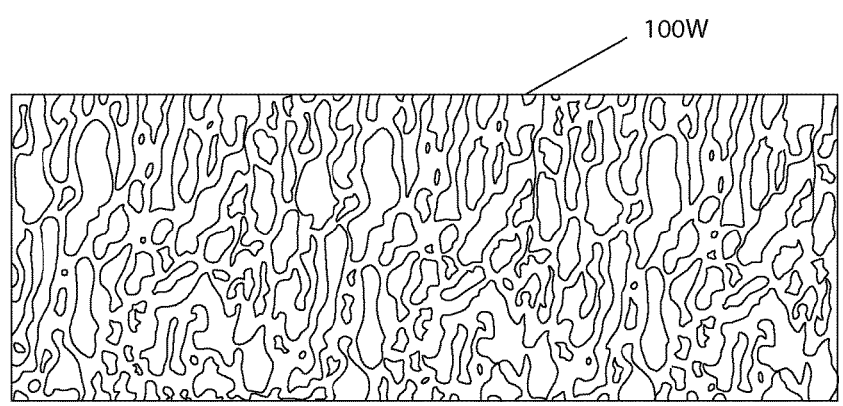
Figures 3A, 3B:
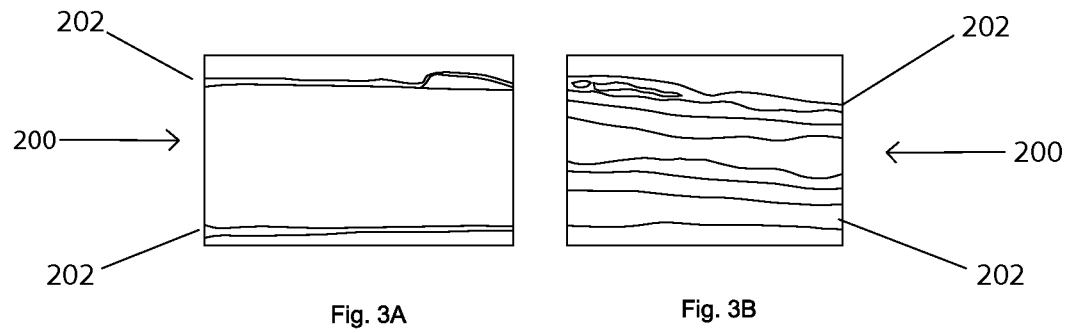
FIGS. 3A and 3B show two longitudinal sections of allograft fiber material after 3 and 6 weeks of culturing with cells according to the state of the art. Differing in magnification, no apparent difference in size was evident despite the much thicker matrix that attached to the NDGA-treated fibrils.

The surface pattern is introduced by etching and/or embossing the surface or surfaces of the biomaterial. The surface pattern provides for a substantially continuous network having voids and enhances the osteo-conductivity of the biomaterial and is a 3-dimensional network. One example of the surface pattern can be derived from FIG. 1. For comparison, FIG. 2A shows a photo of an actual whale bone 100W of the same scale as FIG. 2. The voids and ridges of the actual whale bone 100W remarkably similar to the replication pattern 100A of FIG. 2. The upper left small photo is to scale; the lower left is an enlargement. This ability to mimic a natural and successful bone pattern is believed to be extremely beneficial to achieving enhanced new bone growth on bone implant devices made of plastic or metal implantable materials.

Figure 12:
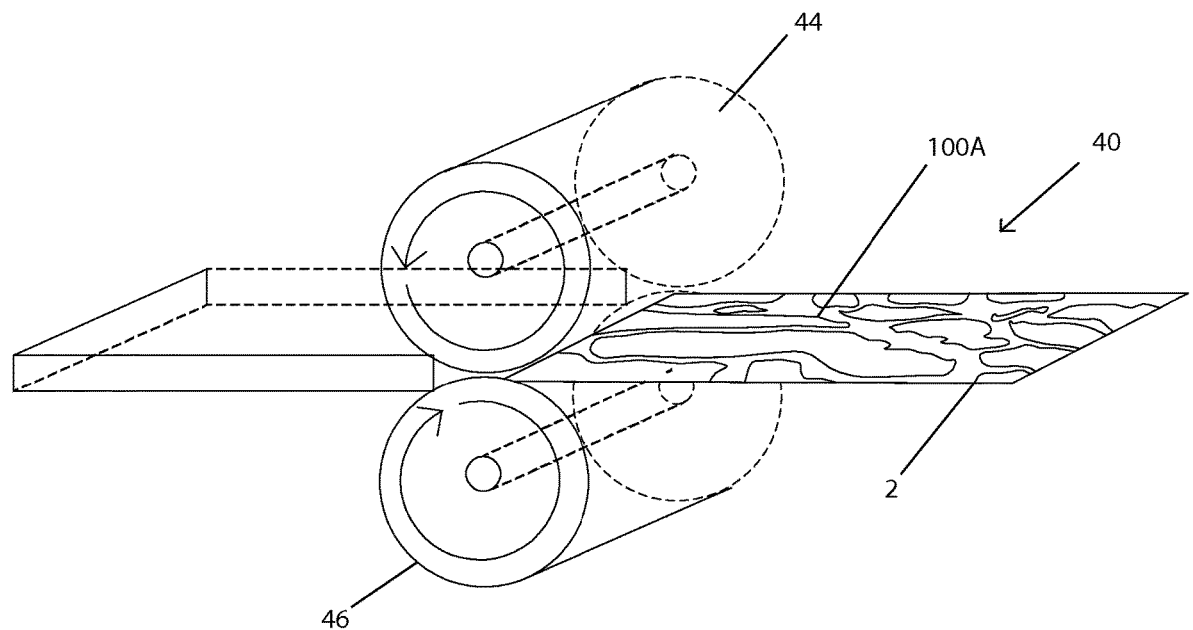
FIG. 12 shows a schematic drawing of a device for producing a sheet material according to the present invention by rolling.
Figure 13:
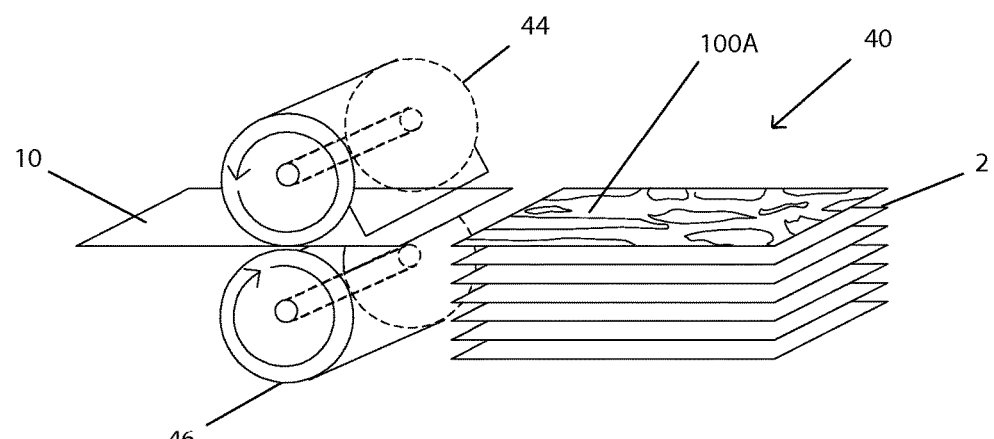
FIG. 13 shows another schematic drawing of the device according to FIG. 12, further equipped for producing thin wafer material for producing a sheet material laminate.

Advancements in technology and refinements in application now permit reproducible templates 100A of collagen to be made with 10-micron resolution. Based on high resolution micro-CT analysis of blocks of whale bone (Microphotonics, Inc., Allentown, Pa.), and Micro-CT Center, UCONN Health Center), planar stacks of material 10 can now be reproducibly made that replicate the cancellous morphology of under-modelled mammalian bone, as shown in FIG. 2, using template 100A driven compression molding derived from patterns I00A detailed (Intelligent Micropatterning, LLC, St. Petersburg, Fla.) and etchings defined in metal masters rollers 44, 46 (Akron Metal Etching, Co., Akron, Ohio) as shown in FIGS. 12 and 13 material 40 can be achieved repeatedly in sheets or layers 40.

This application in one embodiment utilizes type-I collagen matrices that have been cross-linked by a unique process to provide a suitable scaffold for culturing of osteoblasts. The uses of structured allograft, or of the structural properties of the allograft material are considered a primary basis for this technology. As a structural property, the shape, confluence, connectivity, density, porosity and cell stimulation characteristics are considered valuable. Bone is a structure where form dictates functional efficiency. Knowing that bone forms under distraction (tension), it also models under compression. The open architecture of this novel biomaterial is to produce bone specific matrix during incubation, and effect efficient tension at the cell matrix interface to support osteoblast physiology.

Example 1

Collagen preparation: Human placentas that have been screened for HIV and Hepatitis preferably are used as the source of collagen. The preferred human fetal membranes preferably are insoluble amnion, soluble amnion, soluble chorion or combinations of them. Both the amnion and the chorion preferably are cleaned of any blood clots or debris. Collagen preferably is extracted using limited proteolytic digestion with pepsin. In brief, tissue preferably is homogenized in 0.5 M acetic acid, the pH adjusted to 2.5 with HCl and the preparation digested twice with pepsin (10 mg pepsin/gm wet weight tissue) overnight. A combination method of selective precipitation from neutral salt solvent and acid solvents preferably are used to purify the collagen. Purified collagen preferably is reconstituted by dialysis against low ionic strength sodium phosphate buffer (pH 7.2) at 15-17° C. The purity of the type-I collagen preferably is assessed by SDS/PAGE using 4-20% linear gradient Trisglycine gels (Koob T. J. and Hernandez D. J., Biomaterials; 23: 203-212, 2002).

Collagen preferably is produced under semi-confined conditions to yield a rectangular sheet of material 40 approximating 1×2 cm×150 micron in thickness. This sheet 40 of biomaterial will then be run through a roller press 44, 46 that will simultaneously emboss the upper and lower surfaces of the collagen with the prescribed porosity and geometry of under modelled bone I00A as shown in FIG. 12. This material preferably is further dried and stored under vacuum.

Figure 4:
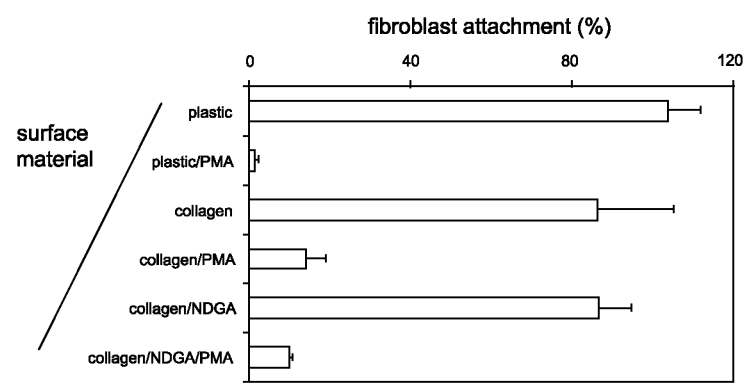
FIG. 4 shows a chart of the fibroblast attachment to tissue-culture treated dishes coated with collagen, and collagen-coated dishes treated with NDGA. The number of cells attached following removal of unattached cells with Dulbecco's PBS measured with CyQuant cell proliferation assay.

NDGA Cross-linking: Modelled collagen sheets preferably are hydrated in 01.M $NaH_2PO_4$, 0.15M NaCl, pH 7.0 (PBS) for 30 minutes followed by treatment with 30 mg/ml NDGA (Sigma Chemical Co., St. Louis, Mo.) as follows: NDGA preferably is suspended in IN NaOH; and then added to the PBS to achieve a final concentration of 3 mg/ml. The collagen sheets preferably are agitated in solution for 24 hours at room temperature, washed in 70% ethanol in water followed by extensive washing with PBS and the NDGA process preferably are repeated. NDGA appears to have no affect on cell attachment with regard to cultured fibroblasts on collagen vs. NDGA-treated collagen as shown in FIG. 4. Direct measurement in osteoblast cultures has not been performed.

In other studies to assess the ability for cells to migrate and proliferate in explant conditions, NDGA-cross-linked fibers were extended through extensor tendons and at specific incubation times up to 9 weeks and assayed for cell number. The number of cells increased throughout the incubation period independent of the cross-linking technology, and the closer to the source of the tissue the greater the number of cells that could be measured (Koob T. J. and Willis T. A., J. Biomed. Mat. Res.; 56: 40-48, 2001).

Excipient Technology: Bioactive factors are critical to influencing the direction, sequence and speed of the regenerative process. Extensive animal and strong clinical data support that osteoinductive growth factors in appropriate dose are sufficient in themselves to effect a biologic response and stimulate bone regeneration. A recent FDA approval of the InFUSE bone graft device would be case in point for data, approval, and regulation of recombinant factors as a device (Department of Health and Human Services, 2. July 2002; http://www.fda.gov/cdrh/mda/does/p000058.pdf).

The inventive scaffold 2 mirrors the surface properties of cancellous bone IO0A as a synthetic analogue fashioned from cross-linked human collagen to enhance cell attachment and matrix deposition, and attenuate matrix factors in deposit that are in themselves osteoinductive through osteoblast priming. Matrix priming, or "pharming", can be extended in application as both a repository and a delivery device, utilizing cell-based delivery systems to effect composition without confounding the delivery with a cell-based system. Through genetic engineering, it is possible to obtain bone matrix tailored to intent without the encumbrance of cells in the delivery system. This strategy profoundly affects the regulatory pathway for gaining market approval and expediting patient treatment. The application teaches to manufacture a mineralized bone matrix that could be used in place of current DMB products, while other devices embody multi-planar laminates 10 of cultured bone sheets 40 to confer 3-D structure. These structures preferably are modular and can be fitted for filing osseous defects in reconstructive efforts, or used as biologic bridges for restoring continuity in defects.

To assure that the matrix deposited on the scaffold 2 and/or sheet material 40 is bone specific, both osteoblasts and mesenchymal stem cells preferably are used to create the bioscaffold 2 matrix. In choosing a cell line suitable for assaying the osteoinductivity of the deposited matrix, it is important that the cells do not in normal culturing conditions spontaneously differentiate into osteoblasts or themselves produce any bone-specific proteins (e.g. alkaline phosphatase). While it is not surprisingly that DBM induces differentiation of confluent human periosteal cells into osteoblast-like cells, the true test of inductivity is demonstrated in that DBM exposure also produces bone-specific response in skeletal muscle myoblast culture.

To validate that the manufactured matrices 2 are engendered with a capacity for osteoinductivity, skeletal muscle myoblast cell lines preferably are used to measure differentiation towards an osteoblast phenotype on the decalcified matrix. The presence of bone-specific proteins during subsequent incubation preferably are interpreted as a response to matrix factors present in the manufactured bone scaffold. Previous work has demonstrated the advantage of spinner flask culture over static culture at 14 and 21 days, in particular enhanced mineralization by convection culturing (Sikavitsas V. I., et al., J. Biomed. Mat. Res.; 62: 136-146, 2002).

Cell culture: Human Osteoblast Cells preferably are obtained from Lonza (Walkersville, Md.) and cultured in alpha-MEM (Gibco/BRL #12561-023) with 1% Pen/Strep (Gibco/BRL=15140-015) and 10% FBS (Hyclone #A-1115-L) at 37° C. in 5% $CO_2$Cells preferably are subcultured every 3-4 days as follows. Cells preferably are washed twice with 5 ml Hanks balanced salt solution without ca- or Mi (BioWhittaker #10-547F, now a division of Lonza) that has been pre-warmed to 37° C. Hanks solution preferably is aspirated and then 2 ml of 0.001% pronase incubated with the cells for 5 minutes at 37° C. Volume preferably is brought to 10 ml with pre-warmed alpha-MEM and a pipette used to dissociate the cells. Cells will then be split 1:10 and carried for additional growth. Induction of phenotype (mineralization) preferably is accomplished by supplementing the media with Hydrocortisone 21 Hemisuccinate and -glycerophosphate as suggested by cell line supplier.

Mesenchymal stem cells (Human Bone Marrow) will also be obtained from Lonza that have been tested for purity by flow cytometry and for their ability to differentiate into osteogenic, chondrogenic and adipogenic lineages. Cells are positive for DC105, CD166, CD29, and CD44. Cells test negative for CD14, CD34 and CD45. Media systems specific to support growth of hMSCs and their differentiation into osteogenic lineage preferably is obtained from the supplier.

Normal human muscle myoblasts (HSMM) preferably is similarly obtained from Clonetics. The cell and media support system advocated by the supplier preferably are used to generate HSMM cultures for the study of cellular development and differentiation. By using three distinct cell lines, it preferably is possible to perform a detailed analysis of synergistic influence of prepared scaffold on mesenchymal cells, and also allow a pure osteoinductivity experiment on non-skeletal cell lines to assay for differentiation and induction.

Cultures preferably are enzymatically lifted from T-75 flasks with 4 ml of trypsin-EDTA solution (0.05% trypsin; Gibco BRL) when they reach 70-80% confluency. Cells preferably are counted and added in a cell suspension drop-wise to the polymer scaffolds. The volume of the cell suspension added to each scaffold preferably is approximately 1 ml, having a cell density of $10^6$ cells/ml. Cells preferably are allowed to adhere to the cell-scaffold constructs for 2 hours and then pieced into 6-well plates and covered with 10 ml of media overnight in the incubator before being placed in the bioreactor. Osteogenic media preferably
is supplemented with 100 nM dexamethasone; 10 mM β-glycerophosphate; and 50 μg/ml ascorbic acid-2-phophate (all from Sigma) (Jaiswal N., et al., J. Cell Biochem.; 64: 295-312, 1997).

The spinner flask system consists preferably of a dual side arm cylindrical flask with a diameter of 58 mm (Belco, Vineland, N.J.) and a No. 12 rubber stopper which will serve as a cover. Three pairs of cell/scaffold constructs preferably are suspended centrally within the spinner flasks. A volume of approximately 120 ml of osteogenic media preferably is added to completely cover the scaffolds, and magnetic stirrer at the bottom of the flask will maintain 30 rpm. Media in all cultures preferably is changed every 2-3 days. Cultures preferably are evaluated at 7, 14, and 21 days for DNA content, Alkaline Phosphatase (ALP) activity, osteocalcin secretion, for calcium deposition and by histology for bone matrix formation.

Analysis: The study can preferably have 4 arms and evaluate the cultured scaffold/cell constructs at time intervals of 7, 14, and 21 days, evaluating: human osteoblasts with fabricated scaffold 2; human mesenchymal stem cells on fabricated scaffold 2; human mesenchymal stem cells on retrieved scaffold 2; human skeletal muscle cells on retrieved scaffold 2 from osteoblast culture.

DNA Measurement: Cellularity of the cell/scaffold constructs preferably is determined using a fluorometric DNA assay (West D. C., et al., Anal. Biochem.; 147: 289-295, 1985). Briefly, scaffolds preferably are removed from the bioreactors at day 7, 14, or 21, washed with double distilled H2O, and homogenized in 1.4 ml of cold 10 mM EDTA, pH 12.3. The homogenates preferably are sonicated for 10 minutes in an ice bath, incubated for 20 minutes at 37° and returned to an ice bath. A volume of 200 µl of 1 M $KH_2PO_4$ preferably is added to neutralize the pH. DNA standards preferably are prepared from stock DNA solutions containing highly polymerized calf thymus DNA (type I, Sigma) at a concentration of 50 µg/ml. A volume of 200 µl of the standard or the homogenized sample preferably is mixed with 1.3 ml of a 200 ng/ml Hoechst 33258-dye (Polysciences, Warrington, Pa.) in a 100 mM NaCl and 10 mM Tris buffer solution. The fluorescence emission at 455 nm preferably is read at an excitation wavelength of 350 nm on a fluorescence spectrophotometer.

ALP activity: AP activity preferably is measured with a commercially available kit (ALP-I 0, Sigma). Scaffolds preferably are placed in centrifuge tube containing 1 ml of a IM
Tris solution at neutral pH and homogenized. The homogenate preferably is added to 1 ml of reconstituted reagent provided by the kit at 30° C. Absorbance preferably is measured every minute for 4 minutes at 405 nm using a HP 8452A Diode array spectrophotometer. The slope of the absorbance versus time preferably is used to calculate the ALP activity.

Osteocalcin secretion: Osteocalcin secreted in the culture media preferably is determined using a commercially available sandwich immunoassay (BT-480) from BTI (Stoughton, Mass.). The BTI Mid-Tact Osteocalcin Elisa Kit is highly specific. It measures both the intact human osteocalcin and the major (1-43) fragment. The assay is a sandwich ELISA which employs two monoclonal antibodies. One antibody (1-19) is immobilized in the wells and the second antibody (30-40) is biotinylated. The assay is highly sensitive (0.5 ng/ml) and requires only a 25 microliter sample. All the necessary reagents, a 96-well strip plate, and a complete 3½ hour protocol are included with the kit.

Calcium deposition: Calcium deposition on the scaffolds preferably are measured by the ortho-cresolphtalein complexone procedure (Sigma Diagnostics, Procedure No. 587). Scaffolds preferably are washed with distilled water, and placed on an orbital shaker to incubate overnight in the presence of 2 ml of 0.5 N acetic acid. Equal volumes of the calcium-binding reagent (0.024% orthocresophtalein complexone and 0.25% 8-hydroxyquinalone) and the calcium buffer (500 mmol/l 2-amino-2-methyl-1,3 propanediol and other non-reactive stabilizers) provided in the assay kit preferably are mixed to generate the assay working solution. A volume of 300 µL of working solution preferably is added to 10 µl of sample in a 96-well plate. To generate a standard curve, serial dilutions of CaCh preferably are prepared (1-250 µg/ml). The plate preferably is incubated at room temperature for 10 minutes and then read at 575 nm. Calcium deposition from each scaffold preferably is reported as mg $Ca^{2+}$ equivalents.

Histology and tetracycline fluorescence microscopy: Scaffolds 2 preferably are immersion fixed in 2% glutaraldehyde, dehydrated in rising concentrations of alcohol and rapidly embedded into plastic for thin sectioning. Sections preferably are stained by Goldner trichrome and Toluidine blue methodology. Mineral deposition preferably is evaluated by adding tetracycline-HCL in the culture media at a final concentration of 10 µg/ml and is a well-established methodology for evaluating matrix deposition. Tetracyline accumulates at bone forming sites and morphometric evaluation preferably 1s carried out using standard Bioquant software on a Nikon E1000 research microscope.

This example demonstrates the utility of imbuing prec1s10n scaffolds with bone specific matrices that could be substituted for human allograft. Conventional strategy for developing repair material for bone has long sought to duplicate the biomechanical characteristics of bone in order to enhance a seamless integration and achieve a rapid restitution of function. In addition to the use of allograft and autograft, substitute matrices of coral, bovine bone and a variety of polymers have been evaluated. Only recently have efforts shifted to seeding osteoblast facilitate attachment. Various shortcomings have accompanied each effort, ranging from poor absorption and fear of viral disease, through outright tissue incompatibility. Regulatory issues for cell-mediated therapies and growth factor delivery also have slowed clinical applications.

The invention shows a departure from those efforts, in that it seeks to specify a scaffold 2 that has been exposed over its course of developments to microgravity. As such, bone cell attachment, loading, and integration will all respond to the dynamic tension of subsequent compressive loading because of it engineered structure, while at the same time the inherent porosity of the scaffold will facilitate matrix enhancement. Fabricating a scaffold carries with it an intrinsic opportunity for biomolecular engineering to manipulate tissue phenotype, or to combine therapeutic additions to normal bone matrix. Using a human collagen matrix that has been cross-linked to assure static structure in culture will enhance the material properties that preferably are stimulated by loading.

Example 2

Figure 5:
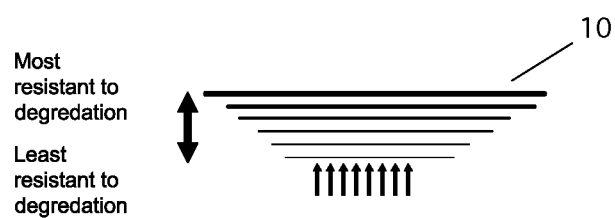
FIG. 5 is a schematic representation of a laminate structured sheet material having different (controlled) degradability.

FIG. 5 shows a poly-laminate of material 10 with specified shape and of pre-determined degradability. In a series of laminar structures with increasing resistance to degradation and with continuity of integral design, a plating system that allowed for not only bridging but also for expansion is envisioned. Given known material thickness and the ability to reconstruct from normal materials using high resolution CT, it is now possible to formulate materials that have specific construction and in purpose simulate under structured bone 100A.

Example 3

The scaffold 2 can be used as a primer for bone formation. Current cadaver sources of allograft bone are insufficient, and revolve around issues of contamination and the mores of harvesting donor tissue. While in principal, profiting from cadaver material is not allowed, not-for-profit operations may have significant operating costs that affect the price-to-patient for use. Alternative sources of autograft are limited in quantity and require operative treatment to obtain. In this invention bio-conductive monolayer matrices 2 preferably are cultured under optimized conditions that result in bone production and mineralization. Materials are then bonded by effective polymerization to create solid materials with known porosity and predictable properties of bone conductivity and inductivity. Cells preferably are removed from the process and the bulk material treated to remove allogeneic components as if it were a "donor" material 2. As a material without cells, the FDA can treat this material as a device, and it should be available for a 510K regulatory status. Cells can be endowed with specific genetic components that will result in enhanced deposition of specific proteins. Proteins such as those in the TGF super family, basic transduction sequences such as the Lim promoter, and other families of growth factors would be considered. As the specific protein of the growth factor rather than the gene for production would be lending itself to the composition, the value of a matrix that had been enhanced would be the consideration. Specific proteins that inhibit vascularization, enhance vascularization, enhance innervation, retard innervation, and other substances that could be secreted are considered.

Example 4

Figure 6:
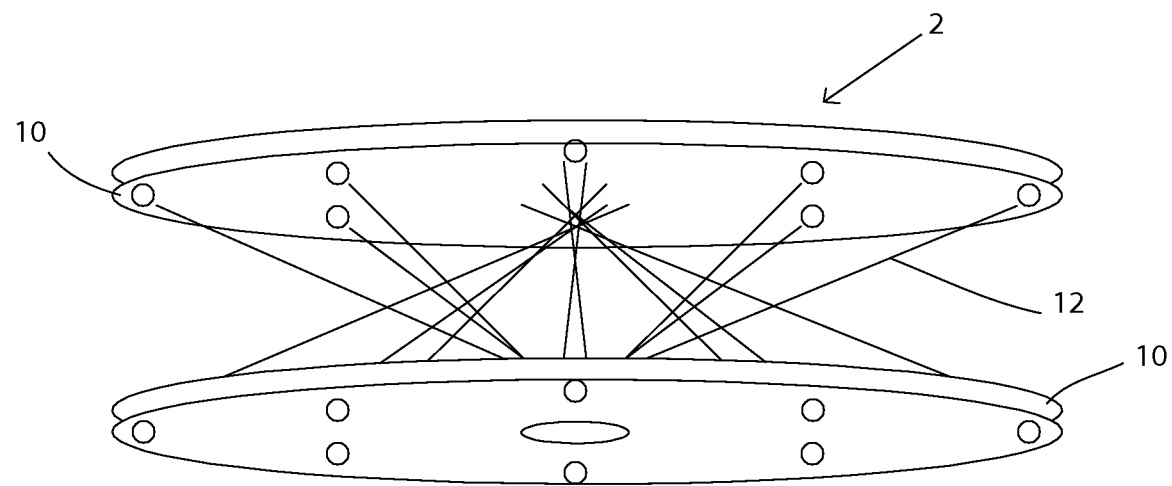
FIG. 6 is a schematic representation of one preferred embodiment of the invention. Two sheet materials are connected by fibers.
Figure 7:
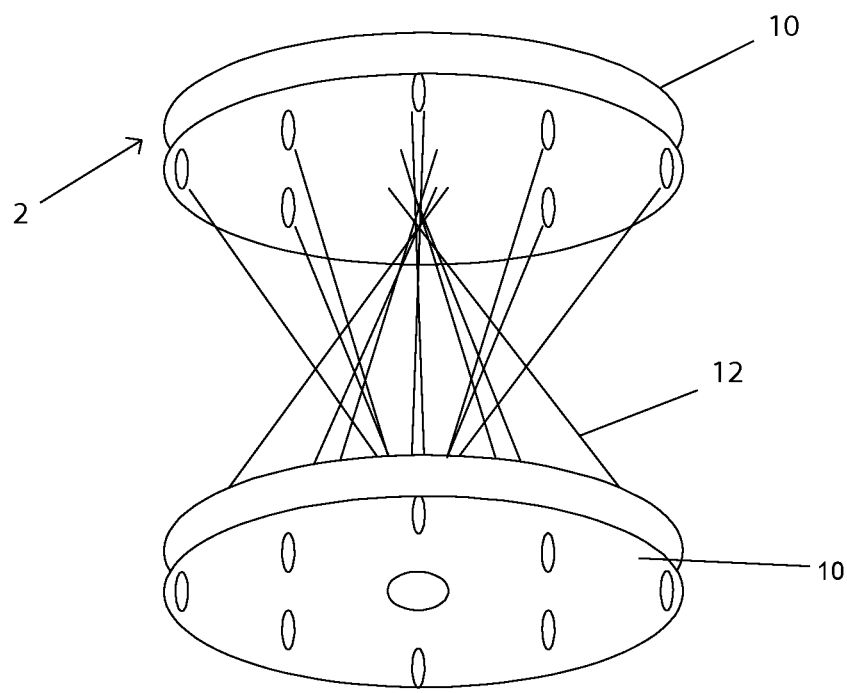
FIG. 7 is a schematic representation of another preferred embodiment of the invention, wherein the void between the sheet material is controlled by the fibers.

For use in articular cartilage repair, the use of structured matrix 2 with defined porosity is considered, as illustrated in FIGS. 5 and 6. Chondrocytes of known genetic make-up preferably are used to define the matrix 2 that is produced. Cells preferably are removed, and matrix preferably is available as generated gel substance.

Each plate 10 would be connected by a series of collagenous fibers 12 that produce tension like spokes on a bicycle or mimics cell microfilaments for supporting cell wall. The FIGS. 5 and 6 represent one "cell" in the construct. Between the parallel plates 10, cells would be allowed to produce matrix 2, and then by cutting fixed templates (trephine, punch-type) defined matrix 2 components could be engineered to size. Heights would be adjustable by the length of the fiber systems 12 used to construct. By seeding with matrix 2, or by creating materials for articulation, this scaffold would permit programmable obsolescence, enhancing progressive load sharing.

Figure 8:
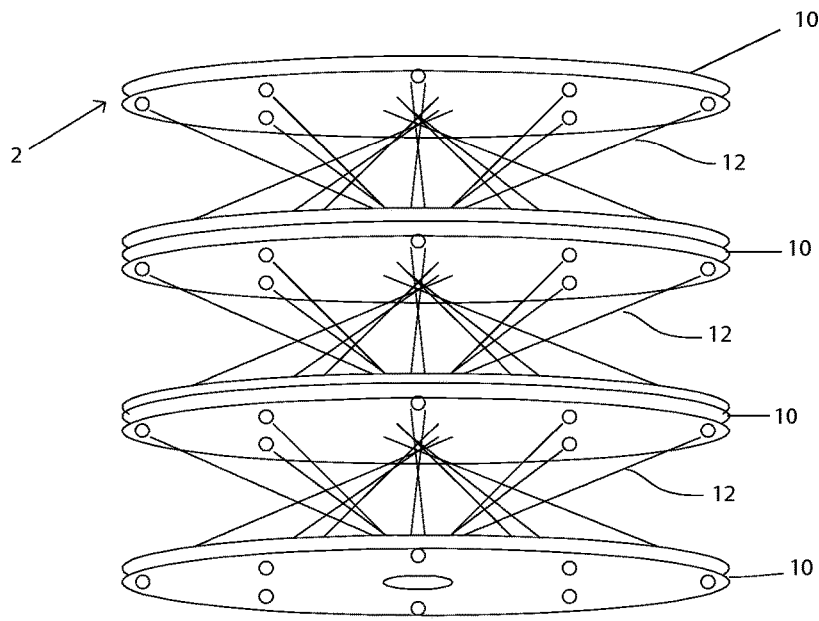
FIG. 8 depicts a schematic representation of another preferred embodiment of the invention, wherein a stack of bone matrix scaffolds according to the present invention is shown.

The fixture of claim is the use of micro-engineered laminates 2 of specified materials that use a cell-based protein production of matrix, as illustrated in FIG. 8. Using both gene-enhanced systems, and in specific conformation, the goal is to engineer a more conductive,
more integrative, stronger and more efficient biologic system. Such design is not limited to either cartilage or to bone systems and the value in creating other specific organs is intended as well. The basic polymer, or collagenous materials could be porous, have sieving properties limited to molecular size and would have defined flexibility. At the current time, degradability is considered an asset in progressive load sharing.

Example 5

Figure 9:
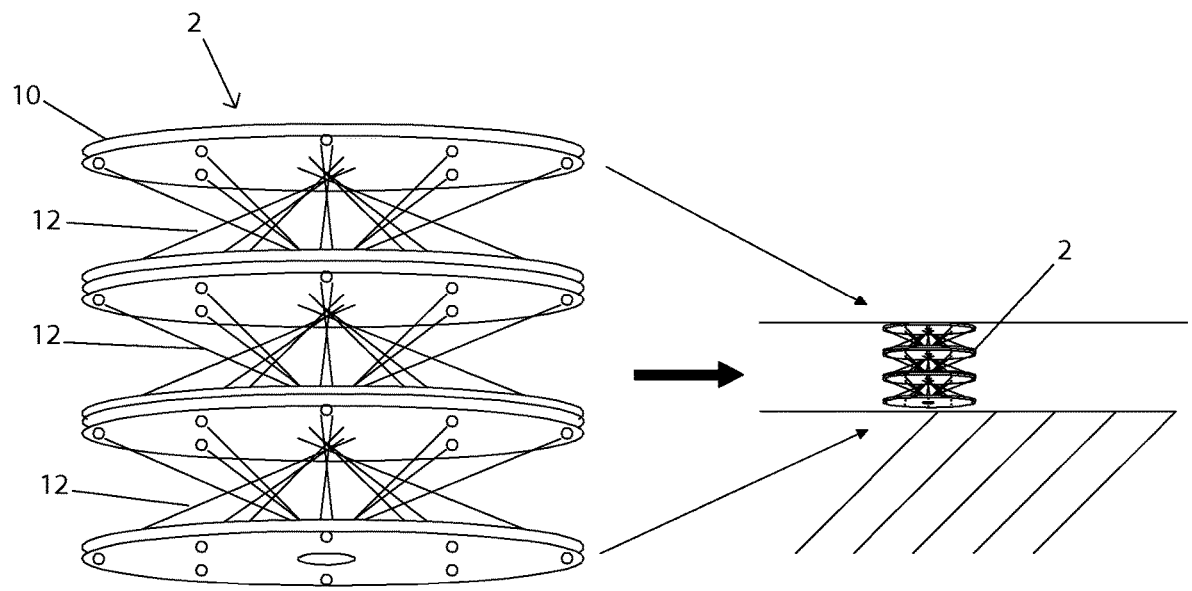
FIG. 9 schematically shows a method for directly implanting the device according to the present invention.
Figure 10A:
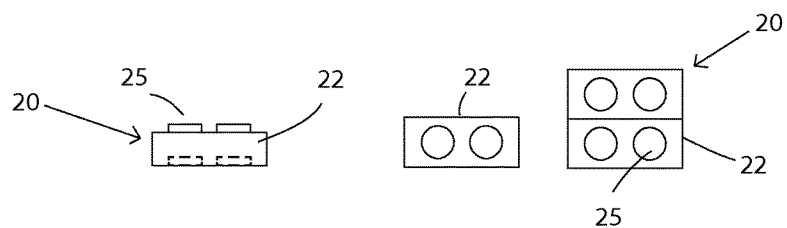
FIG. 10A-10D are schematic drawings of yet another embodiment showing laminates being shaped and connected by interposed tissue blocks.
Figure 10B:
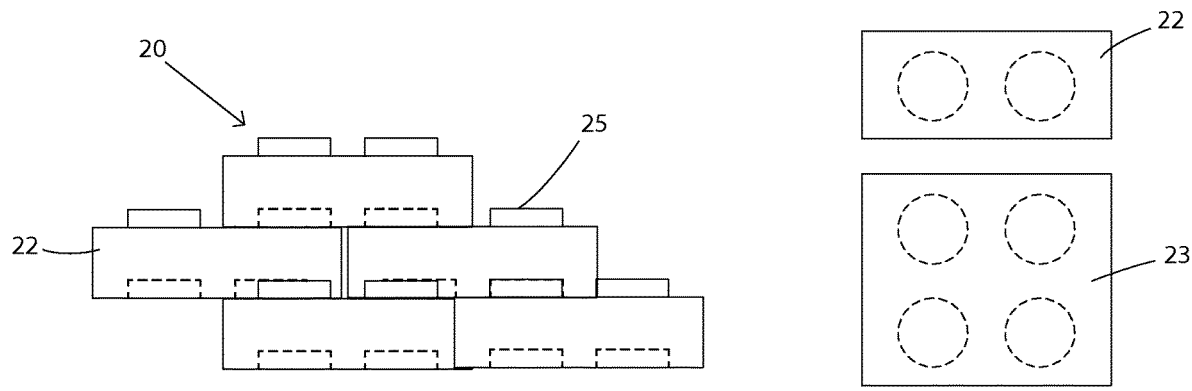
Figure 10C:
Figure 10D:
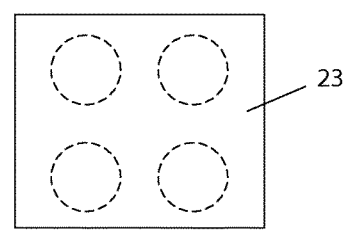

As a fixture for containing autologous cells, the above poly-laminate 2 is considered with defined porous volume, known biomechanical capacity, and an inherent ability to contain cells as shown in FIG. 9. One of the key issues of autologous cell transplantation has been the lack of appropriate containment device. Periosteal covers require additional surgeries, and strategies to directly inject multi-potent stem cells into joints have met with mixed support. In a preferred embodiment of the method according to the present invention, said implanting comprises the direct implantation into the matrix of the bone to be replaced as shown in FIG. 9.

Example 6

The ability to press the laminate 2 and to define form in size and shape is a separate consideration. In defining a series of sheets 10 or 40 of bone, is then possible to press the sheets together to gain a defined form. Defined constructs for facial and cosmetic surgery come readily to mind, and the lack of compatibility issues, the strong role of inductive substances in structure of known micromorphometry, and the off-the-shelf capacity for the substance to integrate make this an ancillary and valuable option. Block materials could either shaped in surgery to defined CAD specifications, or pre-pressed shapes could be utilized as schematically illustrated in figures IOA-1OD. In consideration for material constructs, interlocking blocks 22, 23, 24 of tissues could be assembled (for instance like Lego® block Systems) to create appropriate and approximate contours, using rounded cap 25 pieces to fill the final dimensions of staggered objects. In this consideration, caps 24 and shoulder 26 pieces would be fashioned as well. While the examples in FIGS. 10A-10D are essentially geometric, the shoulders 26 in manufacturing would be best considered arcs to take advantage of the smooth contours. Limitations of the sketches are those of the artist.

Example 7

Figure 11:
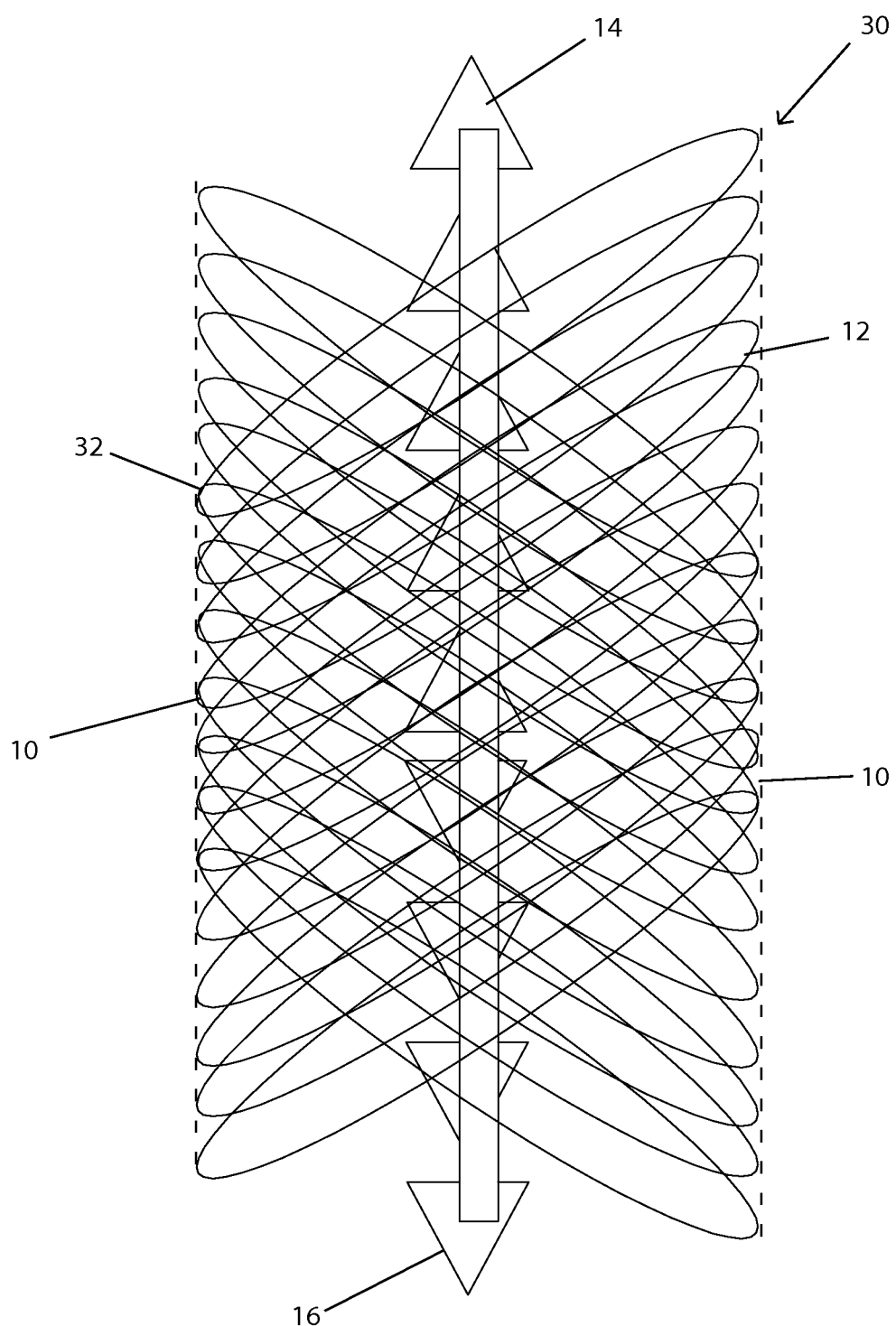
FIG. 11 shows the schematic drawing of an inventive tube-shaped embodiment for bonding and binding two loose ends of tendon material.

A use of material 2 that takes advantage of the properties implies in the tensile tube. Similar to the "Chinese Handcuffs" this would allow the fashioning of collagen fibrils 2 in the braided manner to create a method of bonding and binding two loose ends of tendon material 14, 16 as shown in FIG. 11. The material would be deployed as a loose mesh of fixed diameter in flaccid state, and when pulled would cinch about the free ends of the tendon to effect a manner of binding. Essentially this is a flat braid that is self-tightening. It could be fashioned with a central hollow pleating structure to offer purchase of the two free ends and to allow the outer shroud of material 2 to be deployed.

Example 8

Devices for producing laminate microstructures according to the invention are illustrated in FIGS. 12 and 13. A last aspect of the present invention is then related to a device for producing a sheet material according to the present invention, comprising a device that embosses, etches and/or cuts an osteo-conductive 3-dimensional surface pattern having substantially continuous network having voids into a suitable sheet material. In a preferred embodiment of the present invention, the device according to the present invention comprises compressing rollers as shown in FIGS. 12 and 13. The following description is designed to impart a low-cost efficient use of patterning for making laminate microconstructs. A trademark of Osteotech, Grafton®, a commercially available morselized grafting material or other suitable processed allograft materials are run through a roller 44, 46, much the same as a wringer-type washer apparatus. The rollers 44, 46 are of sufficient hardness as to create and indented surface 100A similar to a pasta cutter, in essence a particular porosity in laminate 40 is achieve by offsetting die-cut mechanisms of the surfaces. This extruding device could be constructed of hard plastic or often suitable material (disposable, sterilizable) and be for immediate use in the operative theatre. It would be lubricated by patient serum and would use the serum adherent as a self adhesive. By using non-proprietary products on approved products, it preferably is possible to more quickly come to market with a designed material. Each roller 44, 46 exists as an embossing press that engenders a pattern 100A of cancellous bone in addition to reducing the sheet 40 to a thin wafer that preferably is part of a laminate 40. Poly-laminate of embossed osteo-inductive material 2. The invention might consist of one or more in a series of rollers 44, 46 that will reduce to a thin size of appropriate porosity, followed by a second set of rollers 44, 46 that will cut in proportion to the diameter of the wheel so that a series of laminates 40 of known architecture can be stacked. Separate from the matrix components 2 this is considered a mechanical device. It would be considered a positive endowment to have serum pushed into the matrix during the initial pressing and them for the porosity developed in the stacking to create a more inductive material 2.

Table 2 is the morphometric data of human cancellous bone samples H-1-H4 and whale cancellous bone WI. Briefly the entire specimen was imaged and the whale bone was purposely cut large to look for the internal consistency of the form to follow variation in scales of sizing. The cancellous bone samples range from 1-4 also in order of being most osteoporotic (1) and the number (4) specimen being the most normal bone. Number 3 specimen is likely an outlier and might sit adjacent to a cortical margin. The whale bone is consistent independent of boundary range or isometric randomization to size. The value in the whale bone is to isotropic distribution, thicker trabecula, greater trabecular spacing, and highest tissue density with lowest connectivity for equalized total volume. The importance is ridge dynamics, higher density with lesser void despite having greater separation makes this an ideal pattern for mimicking to enhance new bone growth in humans.

3-dimensional pattern duplicating or replicating cancellous morphology of under-modelled pre-cancellous bone mimicking a marine or sea mammal bone structure, wherein the repeatable geometric 3-dimensional pattern is repeatably placed on portions of exposed surfaces of the sheet material to create a substantially continuous network having voids formed as a trabecular structure which enhances bone formation, wherein the at least two bone matrix scaffolds are parallel to each other and being connected by a series of collagen fibers arranged in a crisscross pattern between adjacent bone matrix scaffolds, the crisscross pattern similar to spokes pattern on a bicycle tire, wherein the bone graft experience enhanced tensile loading when exposed to normal gravitational forces, wherein said surface pattern is introduced by etching and/or embossing the exposed surfaces of the sheet material, wherein the bone graft further comprises osseous material and/or chondral material.

TABLE 2

| Sample No. | BVF (BV/TV) % | Trab. Thickness μm | Trab. Number 1/mm | Trab. Spacing μm | Connec. Density 1/mm^3 | Apparent Density mg/ccm HA | Tissue Density mg/ccm HA | Total Volume mm^3 | Bone Volume mm^3 | SMI | Bone Surface mm^2 | BS/BV mm^2 | BS/TV 1/mm | BS/MV 1/mm | DA |
|---|---|---|---|---|---|---|---|---|---|---|---|---|---|---|---|
| | | | | | | Just within boundaries of pieces | | | | | | | | | |
| H1 | 14.6% | 142 | 1.41 | 653 | 6 | 65 | 888 | 570.999 | 83.594 | 1.7 | 1595.7 | 19.0 | 2.8 | 3.3 | 1.6 |
| H2 | 21.0% | 146 | 1.69 | 521 | 7 | 149 | 869 | 541.047 | 113.830 | 0.8 | 1989.8 | 17.2 | 3.7 | 4.7 | 2.8 |
| H3 | 24.0% | 191 | 1.65 | 525 | 6 | 185 | 917 | 417.510 | 100.217 | 1.0 | 1399.6 | 13.8 | 3.4 | 4.4 | 1.6 |
| H4 | 31.7% | 156 | 2.24 | 374 | 17 | 286 | 891 | 380.271 | 120.339 | 0.3 | 1908.7 | 15.6 | 5.0 | 7.3 | 1.7 |
| W1 | 21.1% | 183 | 1.20 | 800 | 3 | 190 | 866 | 1070.286 | 225.320 | 0.4 | 3126.6 | 13.7 | 2.9 | 3.7 | 1.4 |
| | | | | | | Smaller isometric cube ROI | | | | | | | | | |
| H1 | 15.9% | 139 | 1.63 | 578 | 6 | 87 | 890 | 70.113 | 11.152 | 1.9 | 208.8 | 18.9 | 3.0 | 3.5 | 1.6 |
| H2 | 24.0% | 150 | 1.80 | 488 | 8 | 186 | 871 | 70.113 | 16.798 | 0.8 | 277.5 | 16.4 | 4.0 | 5.2 | 2.4 |
| H3 | 26.3% | 174 | 1.78 | 487 | 8 | 218 | 911 | 70.113 | 18.451 | 0.9 | 266.0 | 14.4 | 3.8 | 5.1 | 1.7 |
| H4 | 34.6% | 156 | 2.36 | 360 | 18 | 319 | 882 | 70.113 | 24.256 | 0.0 | 372.6 | 15.2 | 5.3 | 8.1 | 1.7 |
| W1 | 21.1% | 167 | 1.29 | 768 | 3 | 226 | 897 | 70.113 | 14.780 | 0.3 | 212.9 | 14.3 | 3.0 | 3.8 | 1.5 |
| | | | | | | Smallest isometric cube ROI | | | | | | | | | |
| H1 | 16.5% | 144 | 1.63 | 577 | 5 | 94 | 892 | 45.084 | 7.457 | 1.8 | 134.3 | 18.1 | 3.0 | 3.6 | 1.6 |
| H2 | 24.9% | 152 | 1.88 | 471 | 8 | 194 | 870 | 45.084 | 11.219 | 0.8 | 180.5 | 16.1 | 4.0 | 5.3 | 2.3 |
| H3 | 26.6% | 173 | 1.82 | 475 | 7 | 221 | 908 | 45.084 | 11.993 | 0.9 | 172.6 | 14.4 | 3.8 | 5.2 | 1.8 |
| H4 | 35.3% | 155 | 2.41 | 352 | 19 | 326 | 880 | 45.084 | 15.903 | -0.1 | 243.7 | 15.2 | 5.4 | 8.4 | 1.7 |
| W1 | 20.4% | 166 | 1.32 | 754 | 3 | 220 | 902 | 45.084 | 9.178 | 0.4 | 134.6 | 14.6 | 3.0 | 3.7 | 1.5 |

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A bone graft comprising at least two bone matrix scaffolds, each of the bone matrix scaffolds having at least one sheet material that has been exposed to microgravity over its development,
   wherein each of said at least one sheet material comprises a surface pattern that enhances osteo-conductivity and supports osteo-inductivity, wherein the surface pattern is a bone-formation-enhancing repeatable geometric 2. The bone graft according to claim 1, wherein said fibers further comprise at least one polymer and/or a mixture of polymers.

3. The bone graft according to claim 2, wherein said at least one polymer is a copolymer having carboxylic acid groups and/or amine groups.

4. The bone graft according to claim 2, wherein said at least one polymer is a conductive polymer selected from polypyrrole, polyaniline, polyacetylene, and polythiophene and mixtures thereof.

5. The bone graft according to claim 1, wherein said fibers are non-aldehyde cross-linked type I collagen.

6. The bone graft according to claim 5, wherein said collagen is chemically cross-linked with nordihydroguaiaretic acid.

7. The bone graft according to claim 1, in the form of a facial and cosmetic surgery graft.

8. The bone graft according to claim 1, wherein said graft is an allograft or autograft.

9. The bone graft according to claim 1, wherein said graft further comprises osteoinductive substances.

10. The bone graft according to claim 9, wherein said osteoinductive substances are bone specific growth factors.

\* \* \* \* \*